United States Patent [19]

Gallop et al.

[11] Patent Number: 5,460,819
[45] Date of Patent: Oct. 24, 1995

[54] METHOD FOR TREATING PQQ-RESPONSIVE HEAVY METAL TOXICITY

[75] Inventors: Paul M. Gallop, Chestnut Hill; Mercedes A. Paz, Brookline, both of Mass.

[73] Assignee: Children's Medical Center Corporation, Boston, Mass.

[21] Appl. No.: 910,608

[22] Filed: Jul. 6, 1992

Related U.S. Application Data

[63] Continuation-in-part of Ser. No. 808,187, Dec. 13, 1991, abandoned.

[51] Int. Cl.$^6$ .......................... A61K 49/00; A61K 31/44
[52] U.S. Cl. .......................................................... 514/292
[58] Field of Search ................................. 514/292, 922; 424/10

[56] References Cited

U.S. PATENT DOCUMENTS

| | | | |
|---|---|---|---|
| 4,898,870 | 2/1990 | Narutomi et al. | 514/292 |
| 5,061,711 | 10/1991 | Urakami et al. | 514/292 |
| 5,075,116 | 12/1991 | LaHaye et al. | 424/617 |
| 5,145,862 | 9/1992 | Aizenman et al. | 514/398 |

OTHER PUBLICATIONS

Gallop et al., "Is the Antioxidant, Anti–Inflammatory Putative New Vitamin, PQQ, Involved with Nitric Oxide in Bone Metabolism?" Abstracts, Connective Tissue Research, #9215015, vol. 27, 1992.
Gallop et al., "Quinone Cofactors In, On and Out of Proteins: Superoxide Removal with Hydrogen Salvaging." (Abstract) Meeting of the Protein Society, 1991.
Flückiger et al. "First Isolation of Methoxatin (PQQ) from Bovine Skim Milk and Other Mamalian Sources." (Abstract) FASEB, Spring Meeting, 1991.
Gallop et al., "Cofactor PQQ in Red Cells, Neutrophils and Biological Fluids, Catalyzes . . . ", (Abstract V–4) Internat'l Symposium on PQQ and Quinoproteins, Nov. 19–22, 1991, Yamaguchi, JP.
Gibbons, "Vitamin or Just Vital?" *Science News*, vol. 139, p. 332, 1991.
Gomez et al., "Evaluation of the efficacy of various chelating agents on urinary excretion and tissue distribution of vanadium in rats," *Toxicology Letters*, vol. 57, pp. 227–234, 1991.
Klinman et al., "Status of the cofactor identity in copper oxidative enzymes," *FEBS Letters*, vol. 282, pp. 1–4, 1991.
McIntire et al., "A New Cofactor in a Prokaryotic Enzyme: Tryptophan Tryptophylquinone as the Redox . . . ", *Science*, vol. 252, pp. 817–823, 1991.
Nishigori et al., "Evaluation of Pharmacological Properties of PQQ," (Abstract V–3) 2nd International Symposium on PQQ and Quinoproteins, Nov. 19–22, 1991, Yamaguchi, JP.
Paz et al., "Specific Detection of Quinoproteins by Redox–cycling Staining," *J. Biol. Chem.*, vol. 266, pp. 689–691, 1991.
Rucker et al., "Pyrroloquinoline Quinone: Effects of Dietary Deprivation on Growth, Connective Tissue . . . , " (Abstract V–2) 2nd International Symposium on PQQ and Quinoproteins, Nov. 19–22, 1991, Yamaguchi, JP.
Sato et al., "Oxyradical Scavenging Activities of PQQ and its Derivatives Against $O_2$ and .OH," (Abstract PIII–2) International Symposium on PQQ and Quinoproteins, Nov. 19–22, 1991, Yamaguchi, JP.
Smidt, et al., "Does the Intestinal Microflora Synthesize Pyrroloquinoline Quinone?" *BioFactors*, vol. 3, pp. 53–59, 1991.
Smidt et al., "Intestinal Absorption and Tissue Distribution of [$^{14}$C] Pyrrolquinoline Quinone in Mice (43219," *Proc. Soc. Exp. Bio. Med.*, vol. 197, pp. 27–31, 1991.
Suzuki et al., "Assay for PQQ in Mammalian Tissues by Gas Chromatography/Mass Spectrometry," (Abstract V–5) 2nd International Symposium on PQQ and Quinoproteins, Nov. 19–22, 1991, Yamaguchi, JP.
Tsuchida et al., "Protective Effect of Oxazolo Pyrroloquinoline (QPQ) Against Experimental Liver Injury," (Abstract V–6) 2nd International Symposium on PQQ and Quinoproteins, Nov. 19–22, 1991, Yamaguchi, JP.
"The Best News of the Year," *Longevity*, pp. 24,26, May, 1991.
Domingo et al., "Chelating agents in the treatment of acute vanadyl sulphate intoxication in mice," *Toxicology*, vol. 62, pp. 203–211, 1990.
Gallop et al., "The Biological Signficance of Quinonoid Compounds in, on, and out of Proteins . . . " *Chemtracts–Biochemistry and Molecular Biology*, 1:357–374, 1990.
Hamagishi et al., "New Biological Properties of Pyrroloquinoline Quinone and Its Related Compounds: . . . , " *The Journal of Pharmacology and Experimental Therapeutics*, vol. 255, pp. 980–985, 1990.
Janes et al., "A New Redox Cofactor in Eukaryotic Enzymes: 6–Hydroxydopa at the Active Site of Bovine . . . , " *Science*, vol. 248, pp. 981–987, 1990.
Kumazawa, et al., "Failure to Verify the Presence of Pyrroloquinoline Quinone (PQQ) in Bovine Plasma . . . , " *Archives of Biochemistry and Biophysics*, vol. 283, pp. 533–536, 1990.
Lawren, "A New Piece in the Aging Puzzle," *Longevity*, vol. 2, pp. 35–37, 1990.
Michaud–Soret et al., "Soybean Lipoxygenases–1, –2a, –2b, and –2c No Not Contain PQQ," *Biochemical and Biophysical Research Communications*, vol. 172, pp. 1122–1128, 1990.
Veldink et al., "Soybean Lipoxygenase –1 is not a quinoprotein," FEBS Letters, vol. 270, pp. 135–138, 1990.
Zychlinski et al., "Inhibitory Effects of Vanadium Pentoxide on Respiration of Rat Liver Mitochondria," *Archives of Environmental Contamination and Toxicology*, vol. 19, pp.

(List continued on next page.)

*Primary Examiner*—Raymond J. Henley, III
*Attorney, Agent, or Firm*—Fish & Richardson

[57] ABSTRACT

Methods are disclosed for treating PQQ-responsive heavy metal toxicity which include the administration of PQQ to a patient in need thereof. The toxicity may be associated with such heavy metals as lead, indium and vanadium.

4 Claims, 2 Drawing Sheets

OTHER PUBLICATIONS

138–142, 1990.

Duine et al., "Quinoproteins, Enzymes with Pyrrolo–Quinoline Quinone as Cofactor," *Annu. Rev. Biochem.* 58:403–26, 1989.

Killgore et al., "Nutritional Importance of Pyrroloquinoline Quinone," *Science*, vol. 245, pp. 797–896, 1989.

Nishigori et al., "Preventive Effects of Pyrroloquinoline Quinone on Formation of Cataract and Decline . . . , " *Life Sciences*, vol. 45, pp. 593–598, 1989.

Richelmi et al., "Multiple Mechanisms of Vanadate–Induced Cell Killing," *Biological Trace Element Research* vol. 21, pp. 331–335, 1989.

Robertson et al., "Spectral Studies of Bovine Dopamine β–Hydroxylase", *The Journal of Biological Chemistry*, vol. 264, pp. 19916–19921, 1989.

Buescher et al., "Antioxidant Properties of Human Colostrum," *Pediatric Research*, vol. 24, pp. 14–19, 1988.

Hobara et al., "Quinone Derivatives Lower Blood and Liver Acetaldehyde but Not Ethanol Concentrations . . . ," *Pharmacology*, 37:264–267, 1988.

Houck et al., "Biosynthesis of Pyrroloquinoline Quinone. 1. Identification of Biosynthetic Precursors . . . ," *J. Am. Chem. Soc.*, vol. 110, pp. 6920–6921, 1988.

Paz et al., "Direct and Amplified Redox–Cycling Measurements of PQQ in Quinoproteins and . . . , " in Jongejan et al., eds. *PQQ and Quinoproteins*, Kluwer Acad. Pub. (Boston), pp. 131–143, 1989.

Watanabe et al., "Protective Effect of Pyrroloquinoline Quinone Against Experimental Liver Injury in Rats," *Current Therapeutic Research*, vol. 44, pp. 896–901, 1988.

Van Kleef et al., "L–Tyrosine is the precursor of PQQ biosynthesis in Hyphomicrobium X," *FEBS*, vol. 237, pp. 91–97, 1988.

Hansen et al., "Hemolytic Activity of Vanadylsulphate and Sodium Vanadate," *Acta*, vol. 59, pp. 562–565, Supplement VI, 1986.

Büchi et al., "A Synthesis of Methoxatin," *J. Am. Chem. Soc.*, vol. 107, ppp. 5555–5556, 1985.

Nechay, "Mechanisms of Action of Vanadium," *Ann. Rev. Pharmacol. Toxicol*, 24:501–524, 1984.

Jones et al., "Chelate Antidotes for Sodium Vanadate and Vanadyl Sulfate Intoxication in Mice," *Journal of Toxicology and Environmental Health*, vol. 12, pp. 749–756, 1983.

Gainor et al., "Synthesis of the Bacterial Coenzyme Methoxatin," *J. Org. Chem.*, vol. 47, pp. 2833–2837, 1982.

Vyskocil et al., *The Lancet*, pp. 1078–1079, May 8, 1982.

Jung et al., *The Journal of Organic Chemistry*, vol. 47, pp. 1148–1150, 1982.

Gainor et al., *The Journal of Organic Chemistry*, vol. 46, pp. 4317–4319, 1981.

Corey et al., *Journal of the American Chemical Society*, vol. 103, pp. 5599–5600, 1981.

Salisbury et al., *Nature*, vol. 280, pp. 843–844, 1979.

METHOD FOR TREATING PQQ-RESPONSIVE HEAVY METAL TOXICITY

This invention was supported at least in part by funding from the United States government, and the government has certain rights in the invention. This application is a continuation in part of commonly owned U.S. Ser. No. 07/808,187 filed Dec.13, 1991, now abandoned hereby incorporated by reference.

This invention relates to compositions and therapeutic methods comprising 2,7,9,-tricarboxypyrroloquinoline Quinone (which we will refer to as "PQQ" for convenience, and which is sometimes also known as methoxatin) and related compounds including redox forms of PQQ.

PQQ was isolated in 1979 from methylotrophic bacteria. The structure of a crystalline acetone adduct of PQQ was elucidated by X-ray diffraction (Salisbury et al., 1979, Nature 280:843-844), and the organic synthesis of methoxatin has been described (Corey and Tramontano, 1981, J. Am. Chem. Soc. 103:5599–5600; Gainor and Weinreb, 1982, J. Org. Chem. 46:4317–4319; Hendrickson and deVries, 1982, J. Org. Chem. 47:1148–1150; Gainor and Weinreb, 1982, J. Org. Chem. 47:2833–2837; Buchi et al., 1985, J. Am. Chem. Soc. 107:5555–5556). The entire carbon and nitrogen skeleton of tyrosine (a metabolic precursor of PQQ) is incorporated into PQQ, probably through a dopaquinone intermediate (van Kleef and Duine, 1988, FEBS Lett. 237:91–97), and the remainder of PQQ is most likely derived from glutamic acid (Houck et al., 1988, J. Am. Chem. Soc. 110:6920–6921).

PQQ is the redox factor in several bacterial enzymes (oxidases) from which it can be removed by dialysis. It is reported to be covalently bound to some mammalian enzymes in which case the complex has been designated as a quinoprotein (Duine and Jongejan, 1989, Ann. Rev. Biochem. 58:403–426), a term that describes enzymes purported to contain covalently bound PQQ. However, several investigations do not confirm the occurrence of covalently bound PQQ in mammalian enzymes (Gallop et al. (1990) Chemtracts—Biochemistry and Molecular Biology 1: 357–374; Robertson et al., 1989, J. Biol. Chem. 264:19916–19921; Paz et al., 1991, J, Biol. Chem. 266:689–692; Veldink et al., 1990, FEBS Lett. 270:135–138; Michaud-Soret et al., 1990, Biochem. Biophys. Res. Comm. 172:1122–1128; Kumazawa et al., 1990, Arch. Biochem. Biophys. 283:533–536; Klinman et al., 1991, FEBS Lett. 282:1–4). Recent work has led to the identification of the posttranslationally derived redox-cofactor, 6-hydroxydopa quinone, in bovine plasma amine oxidase (Janes et al., 1990, Science 248:981–987), and of another type of covalently bound posttranslationally derived quinone in the bacterial methylamine dehydrogenase (McIntire et al., 1991, Science 252:817–824).

In another study, when mice were fed a chemically defined diet devoid of PQQ, they grew poorly, failed to reproduce and became osteoarthritic (Killgore et al., 1989, Science 245:850–851). The presence of PQQ in the biological fluids of higher organisms is evidenced by its ability to efficiently support glycine-driven redox-cycling (Gallop et al., (1990) Chemtracts, cited above; Paz et al., 1989, In: PQQ and Quinoproteins, Jongejan and Duine, eds. Kluwer Academic Publishers, Norwell, Mass., pp 131–143).

PQQ has been implicated in: 1) antioxidant protection against glucocorticoid-induced cataract accompanied by maintenance of reduced glutathione levels (Nishigori et al., 1989, Life Sci. 45:593–598); 2) protection against hepato-toxin-induced liver injury (Watanabe et al., 1988, Curr. Therap. Res. 44:896–901; Urakami et al. U.S. Pat. No. 5,061,711); 3) acceleration of ethanol detoxification by augmented acetaldehyde oxidation (Hobara et al., 1988, Pharmacology 37:264–267); 4) antiinflammatory action against carrageenin-induced rat paw edema (Hamagishi et al., 1990, J. Pharmacol. Exp. Therap. 255:980–985); and 5) control of NMDA receptor-mediated neuronal injury (Aizenman et al. U.S. patent application Ser. No. 07/758, 576), hereby incorporated by reference.

It is not known whether PQQ is synthesized by the intestinal microflora (Smidt et al.,1991, Biofactors 3:53–59). However, free PQQ is readily absorbed in the intestine (Smidt et al., 1991, Proc Soc. Exp. Biol. Med. 197:27–31). Human colostrum reportedly contains a heterogeneous antioxidant activity which differs from ascorbate and other known antioxidants (Buescher and McIlheran, 1988, Ped. Res. 24:14–19).

In Harvard Medical Area FOCUS, November 8, 1990, there is speculation that PQQ can be useful in treating numerous diverse diseases: inflammatory joint disease, hemolytic anemia, and neuromotor defects. PQQ is reportedly found in mammalian fluids, including blood, cerebrospinal fluid, urine, adrenal gland extracts, and milk. PQQ is also reported to detoxify noxious substances and to protect cells against oxidative stress injury.

SUMMARY OF THE INVENTION

Our findings relative to PQQ give rise to an invention having several aspects discussed below.

I. Administration of PQQ with a Reducing Agent

One aspect of the invention features therapeutic compositions comprising PQQ in combination with reducing agents described below which are sufficient to maintain PQQ in a reduced state. Such compositions exhibit substantial advantages over other PQQ formulations. As described below in more detail, PQQ can be reduced in biological fluids (by one reducing equivalent) to its semiquinone [PQQ(H)·], which in turn can be further reduced to the hydroquinone [PQQ (2H) ].

The quinone form of PQQ reacts with a variety of nucleophilic compounds present in biological fluids, forming undesired adducts with amino acids and with certain protein side chains such as —SH and —NH$_2$. In addition, thiolquinolation (the process of air oxidation of catecholamines forming undesired quinonoid compounds that react with thiol groups in protein) is accelerated by PQQ in the absence of excess reducing equivalents.

To avoid formation of amino acid or protein adducts, or thiolquinolation, the invention features compositions and methods in which PQQ is administered with a substantial excess of a reducing agent or a combination of reducing agents that is characterized by a redox potential adequate to maintain extracellular PQQ substantially in reduced form. One preferred redox couple is the ascorbate ("ASC$^-$") ⇌ semidehydroascorbic acid ("ASC·") couple. PQQ and ascorbate co-operate in a redox cycle as follows:

$$H^+ + PQQ + ASC^- \rightleftharpoons PQQH· + ASC·$$

Other specific reducing agents and their cycles, as well as the context and significance of these cycles, are explained in greater detail below.

This aspect of the invention represents a general improvement to PQQ therapies, in that it avoids side effects and enhances availability of PQQ to accomplish the desired effects. This aspect of the invention not only improves various existing PQQ therapies involving PQQ, it also improves various therapies which are proposed here for the first time and which are the subject of other aspects of the invention, as discussed below. Specifically for central nervous system applications, the reduced form of PQQ is transported across the blood brain barrier more efficiently than the oxidized form. In general, it is also advantageous that the reducing agent can act to shuttle electrons between an aqueous system (e.g., intracellular medium) and a non-aqueous system (e.g., within a lipid membrane). To illustrate, anionic PQQ redox compounds and ascorbate are water soluble under physiological conditions; uncharged semidehydroascorbic acid will dissolve in non-aqueous systems, where it can obtain its electron to form ascorbate anion which will be partitioned into the aqueous phase.

In summary, a first aspect of the invention generally features therapeutic physiologically acceptable mixtures comprising PQQ and at least one reducing agent (i.e., a single reducing agent or a combination of reducing agents) characterized by a net reducing capacity higher than the oxidizing capacity of PQQ originally present in the mixture. The reducing agent(s) are originally present in substantial molar excess of the PQQ content. In other words, if the mixture is formed from the oxidized (quinone) form of PQQ, and the reducing agent is added, then the amount of the reducing form of the reducing agent added is in substantial molar excess to the amount of original PQQ. This aspect of the invention also features kits for forming such mixtures comprising a supply of stably maintained PQQ (preferably in the oxidized form), and a supply of the reducing agent, separately packaged from the supply of PQQ. Finally, this aspect of the invention features therapeutic treatments using such mixtures.

Preferably, the reducing agent is ascorbate with a suitable cation (most preferably sodium ascorbate). Alternative reducing agents include anionic reductone (-ene diol) compounds such as Tiron® (4,5-dihydroxy-1,3-benzenedisulfonic acid, as the disodium salt) and other dihydroxy sulfonates, as well as thiol or sulfhydryl-containing compounds such as D-penicillamine and mercaptosuccinate. Still other reducing agents include glycine and dopamine. Also preferably, the kit includes a supply of PQQ in solid form, and a supply of a molar excess of the reducing agent(s) in solid form. Conditions that can be treated according to this aspect of the invention include: a) toxic oxidative stress; b) lipid peroxidation; c) toxicity associated with heavy metals; d) side effects associated with administration of anthracycline antitumor agents; e) effects of ionizing radiation; f) red cell disorders with methemoglobinemia; g) generation of toxic radical oxidants by agents including xenobiotics such as viologens, NTPT (see below), streptozocin, alloxan, and others; h) sustained requirement for hyperalimentation; i) inflammatory disease; j) ethanol toxicity, particularly that associated with removal of acetaldehyde; k) cataracts; and l) glutamate mediated neuronal toxicity.

II. Treating Specific Disorders With PQQ

We have also realized that PQQ can be an effective therapeutic for various conditions that have not previously been recognized as amenable to PQQ treatment. Therefore, yet other aspects of the invention feature treating specific disorders with PQQ (whether or not a reducing agent is included with the PQQ): a) toxic oxidative stress; b) lipid peroxidation; c) toxicity associated with heavy metals; d) side effects associated with administration of anthracycline antitumor agents; e) effects of ionizing radiation; f) red cell disorders with methemoglobinemia; g) generation of toxic radical oxidants by agents including xenobiotics such as viologens, NTPT (see below) streptozocin, alloxan, and others; h) sustained requirement for hyperalimentation.

Other advantages and features of the invention will be apparent from the following description of the preferred embodiments and from the claims.

DESCRIPTION OF THE PREFERRED EMBODIMENT(S)

I. Combining PQQ with a reducing agent

One aspect of the invention features kits, therapeutics and methods of therapy which combine PQQ with a reducing agent. While not wishing to be bound to any specific mechanism, we will briefly describe the molecular interrelationship between PQQ and reducing agent(s). We believe the interrelationship between PQQ and the reducing agent(s) is responsible to a significant degree for the benefits realized by this aspect of the invention.

A. The Redox interrelationship between PQQ and a Reducing agent PQQ has various desirable effects as a result of intracellular reactions detailed below. Particularly important reactions involved in redox cycling of PQQ and superoxide (FIG. 5), and redox cycling of PQQ with methemoglobin (FIG. 6), are discussed below. In order to realize therapeutic benefits from these reactions, PQQ is administered so as to increase extracellular levels of PQQ. The extracellular reduced PQQ, after being internalized by cells, will increase cellular levels of PQQ in various redox states which will be dictated by the intracellular environment and those intracellular PQQ redox compounds will participate in the desired reactions described below.

The need for co-administration of a reducing agent with PQQ can be understood with reference to extracellular events resulting from introduction of a bolus of PQQ. In biological fluids, prior to the exogenous introduction of a bolus of PQQ, concentrations of ascorbate (the compound which we believe is naturally responsible for maintaining PQQ in its reduced form) generally exceed those of PQQ by several orders of magnitude. Whereas adult serum concentrations of PQQ are 100–400 nanomolar, ascorbate concentrations are generally millimolar or more (e.g., 0.1–1 mM). Thus, ascorbate concentrations typically exceed PQQ concentrations 1000-to 10,000-fold. In spinal fluid the ratio of ascorbate to PQQ exceeds that in serum by as much as another order of magnitude. It is also estimated that ascorbate present is generally present with the ascorbic anion in great excess (10:1) over dehydroascorbate, its oxidized form.

At pH 7, the standard redox potentials of PQQ/PQQ(2H) is reported to be about +90 mv (NHE) (see Eckert et al., (1982) *Proc. Nat'l . Acad. Sci. U.S.A.* 79:2533–2536) and that of dehydroascorbate/ascorbate is about +60 mv. The reversible cycling reaction at issue can generally be represented as follows:

$$H^+ + PQQ + ASC^- \rightleftharpoons PQQH + ASC^-$$

A bolus of oxidized PQQ, without concomitant addition of additional reducing equivalents, could overwhelm the endogenous extracellular reducing agents, resulting in additional extracellular amounts of the oxidized (quinone) form of PQQ. PQQ in the quinone form reacts with a variety of nucleophilic compounds present in biological fluids forming adducts with amino acids and with certain protein side chains. Some of the adducts form irreversibly and much of the PQQ administered through a bolus injection could be lost before the ascorbate present in biological fluids could reduce it to less reactive PQQ(2H). Accordingly, PQQ should generally be administered present with a large excess of a reducing agent such as sodium ascorbate.

Furthermore, aerobically, PQQ catalyzes the oxidation of ascorbate with formation of dehydroascorbate. Thus, it is important that PQQ and excess sodium ascorbate be mixed shortly before administration. Premixed ascorbate-PQQ kept free of air can be used, but it is generally easier to mix PQQ and sodium ascorbate shortly before administration.

Figure 1:
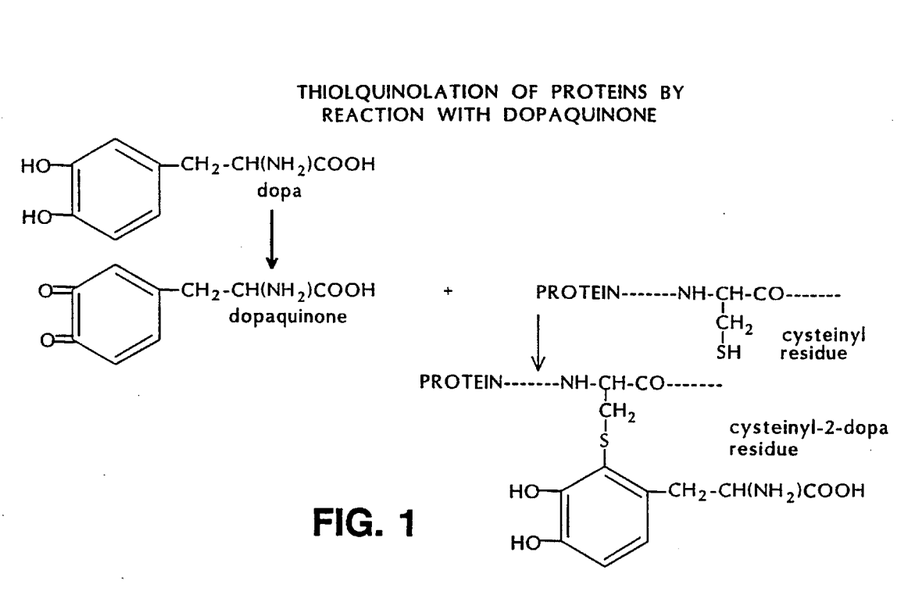
FIG. 1 is a diagram of certain redox reactions involving PQQ.

It is also important that catechols and catecholamines are very sensitive to oxidation and to both the presence of PQQ and ascorbate. Catecholamines, if not protected against air oxidation by ascorbate, form quinonoid compounds that react with thiol groups in proteins. Itoh et al. (1988) *Biochem. Pharmacol.* 37:1707–1710. This process, known as thiolquinolation, is accelerated by PQQ when excess To illustrate this point, human serum can be freed of ascorbate, catecholamines and PQQ by dialysis. Addition of dopa and exposure to air after dialysis leads to the thiolquinolation of the serum proteins. Thiolquinolated proteins, separated by SDS-PAGE and electroblotted to nitrocellulose react as quinolated proteins and can be detected by redox cycling as described by Paz et al., (1991) *J. Biol. Chem.* 266:689–692. Thiolquinolation is accelerated by PQQ added to the dialyzed serum protein along with dopa. However, the addition of excess sodium ascorbate to dialyzed serum prevents thiolquinolation by dopa and other catechols/catecholamines with the maintenance of free protein sulfhydryl groups. Excess thiol compounds added to the dialyzed serum proteins are also protective, but ascorbate is the more effective and non-toxic anti-thiolquinolation reagent. The chemistry is depicted in FIG. 1.

First dopaquinone is formed from dopa: 1) by spontaneous oxidation in air; or 2) by accelerated oxidation with PQQ present. Oxidation is prevented by ascorbate anion. Dopaquinone then reacts with protein as shown. Note that the reaction shown in FIG. 1 can also occur on the 5-position of dopa. Two protein chains can also be crosslinked by a reaction on both the 5 and 2 positions.

Thiolquinolation generates proteins which contain cysteinyl-2-S-dopa and cysteinyl-5-S-dopa residues, as well as proteins containing cysteinyl-2-S-dopa-5-S-cysteinyl crosslinks. Thiolquinolation leads to the inactivation of enzymes which contain functionally important cysteinyl residues and free sulfhydryl groups. Accordingly, it is best to administer PQQ as PQQ(2H) in an excess of reducing agent such as sodium ascorbate or one of the other reducing agents discussed above. Under these conditions PQQ(2H) is virtually free of toxicity to cells at tissues even in pharmacological concentrations.

In sum, suitable reducing agents operate to cycle PQQ between reduced and oxidized forms. A bolus of PQQ, even if initially in reduced form, will be transformed in vivo to yield a substantial extracellular amounts of oxidized PQQ if adequate levels of reducing agent are not maintained. Extracellular build-up of the oxidized, quinone form of PQQ has undesirable consequences. This aspect of the invention reduces these undesired consequences.

B. Useful Reducing Agents

By far the preferred reducing agent for use in the invention is ascorbate in combination with a physiologically compatible anion such as $Na^+$ or $K^+$ or $Ca^{2+}$. These compounds are commercially available, and they can be compounded into physiological mixtures by procedures well known to those in the field. Our research indicates that the PQQ/ascorbate redox cycling system is in fact the system that occurs naturally, and that the use of ascorbate to control the redox state of exogenously added PQQ therefore mimics natural events.

Even if the above mechanism is not entirely descriptive of natural events, however, ascorbate is a particularly beneficial reducing agent for use in this invention. It is physiologically compatible, it has the appropriate reducing power relative to PQQ, it can be formulated into useful therapeutic compositions, and it is readily available and virtually non-toxic in reduced form.

Figure 3:
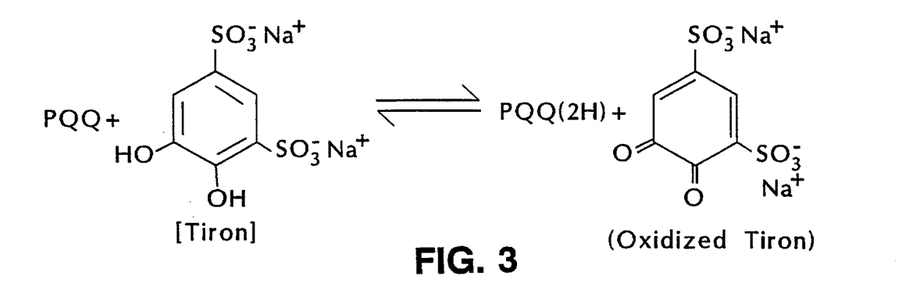
FIG. 3 is a diagram of the tiron redox couple.
Figure 4:
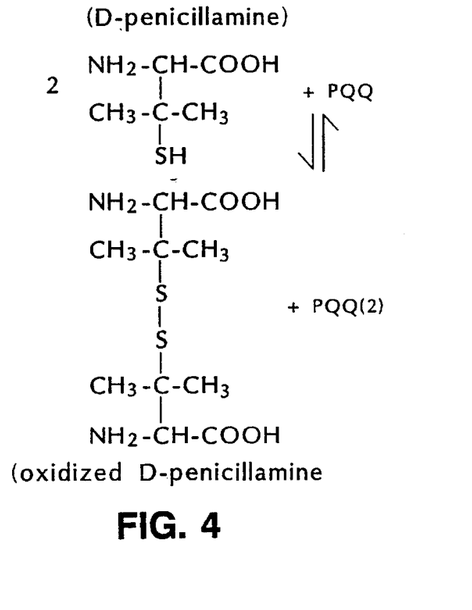
FIG. 4 is a diagram of the penicillamine redox couple.

Those skilled in the art will realize, however, that other reducing agents may also fulfill the above criteria, making them useful for the practice of the invention, as described below. For example, Tiron® or other physiologically acceptable anionic hydroquinones, and D-penicillamine or other physiologically acceptable thiol or sulfhydryl-containing compounds (particularly amino acids, including mercaptosuccinate) are suitable reducing agents for use in the invention. Glycine and dopamine are also acceptable and readily available. The redox couples for two of those compounds are shown in FIG. 3 and FIG. 4, respectively, and the ability of those compounds to provide the benefits of the invention is understood by reference to the above discussion of ascorbate. In particular, physiologically acceptable compositions of these compounds (which, inter alia, are chelating agents to treat heavy metal poisoning) can be used in the invention. D-penicillamine is also known as a therapy for Wilson's disease and for rheumatoid arthritis. Tiron® is particularly known for its use as a therapy for vanadium poisoning. As mentioned above, where the reducing agent has a separate desirable effect in a specific PQQ-related therapy (e.g., to chelate the toxin at issue), its use as a reducing agent for PQQ is particularly beneficial.

C. Kits and Mode of Administration

The above-described PQQ/reducing agent combinations should be formulated to provide a substantial molar excess of reducing agent, for example, about 1–100mg (preferably 5–20mg) PQQ per kg body weight per day and about 5mg–1g (preferably 20–70mg) NaASC per kg body weight per day. Any physiologically acceptable buffer can be used, such as phosphate buffered saline solution (pH ~7.4). PQQ is stored as a dry powder in its more stable, oxidized form. The NaASC is stored as a dry powder. Both powders are mixed with the buffer at the time of use. Typically the mixture would be about 0.05–5 mM with respect to PQQ and 0.2–15 mM with respect to NaASC.

The combination may be formulated for injection by any suitable route (e.g., i.p., i.v.). Alternatively, the combination may be formulated for oral administration, where the patient's condition permits. Where local, rather than systemic treatment is preferred, it is possible to administer the complex locally by various known methods including controlled release polymer implants. In particular, due to the negative charge on the components, iontophoresis can be used. Typically, dosages will be repeated several times daily.

Kits for such formulations include a sealed dry supply of PQQ and a sealed dry supply of NaASC or other suitable reducing agent. Optionally, a supply of buffer (PBS) in an amount suitable for formulation with the dry ingredients is also included. Such kits are readily formulated from suitable grades of reagents. PQQ is available commercially from Fluka of Switzerland (as PQQ.2Na). NaASC is available from numerous sources.

Other reducing agents including Tiron® is available as described by JP Pat. 4327 (Sanwa Pure Chem., Chem Abstr. 48:5215c (1954) and from Aldrich Chemical Co. D-penicillamine, glycine, dopamine, and mercaptosuccinate are also available from Aldrich. Those agents can be formulated into aqueous mixtures in a manner similar to that discussed above. In general, weights of Tiron® used will be greater than weights of NaASC, and weights of D-penicillamine and similar compounds will be lower.

II. Therapeutic Indications

A. Oxidative Stress

There are numerous disease states which operate by a mechanism that includes oxidative stress: destruction of tissue by the build-up of toxic radical oxidants, which are derived from the superoxide radical $O_2^-$. An important aspect of the invention is best understood after a review of the chemical reactions involved.

PQQ is a crucially important redox mediator in complex NAD(P)H oxidase reactions. NADPH oxidases are required for the antimicrobial respiratory burst reaction in phagocytic cells (Bellavite (1988) *Free Radical Biol. Med.* 4:225–262) and in a complex related reaction, catalyzed by nitric oxide synthase present in endothelium and in many other cells and tissues (Ignarro (1990) *Ann. Rev. Pharmacol. Toxicol.* 30:535–560). We have isolated PQQ from red cells and neutrophils, and we conclude that PQQ is a key part of a potent antioxidant system which naturally controls oxidative stress injury by helping cells remove toxic oxidants and to help them maintain appropriate cellular levels of reduced glutathione ("GSH") and other important reducing compounds such as NAD(P)H. In sum PQQ (in combination with ascorbate) appears to be an extremely significant natural protection against oxidative injury in living cells. The following discussion explores the implications of our findings.

A major function of PQQ in animal cells is PQQ's catalysis of the reversible interconversion of dioxygen and superoxide ($O_2^-$; also designated "SO"), as shown schematically by Formula 1 below:

$$2H + 2O_2 \leftarrow PQQ \rightarrow 2H^+ + 2 O_2^- \qquad 1$$

Here, 2H represents reducing equivalents derived from cellular metabolism, for example, by glucose oxidation, and 2H is generally present in cells as $NAD(P)H + H^+$, $FAD(H_2)$ (reduced flavins) and by GSH. From formula 1., it follows that excess reducing equivalents, high oxygen tension and higher pH, favor formation of superoxide (SO), a radical redox substance which initiates the formation of toxic radical oxidants unless it is removed rapidly and non-toxically. Alternatively, lower concentrations of reducing compounds, lower pH and lower oxygen tension, result in the oxidative removal of SO, catalyzed by PQQ with the salvage of the reducing equivalents that were used in the production of SO.

The rates of both reductive SO formation and SO oxidative removal depend directly on the concentration of PQQ. The net direction of the dynamic equilibrium expressed by Formula 1, depends on the inherent metabolic commitment of the specific cells involved and their overall redox status. In general, many cells, especially red cells, are poised for superoxide removal where reaction 1 proceeds to the left. However, phagocytic cells such as activated neutrophils, appropriately stimulus-triggered by microbial-membranes, phorbol esters (PMA) or specific hormone-like peptides, become committed to SO-production of superoxide and formation of toxic oxidants used to kill bacteria or other cells which they sense as foreign, and the reaction expressed as Formula 1 proceeds to the right.

In view of SO's toxicity, it has been assumed that there are natural mechanisms for SO removal. The classical understanding of superoxide removal is based on the discovery of enzymes that rapidly dismutate, but do not oxidize, superoxide. An enzyme that dismutates superoxide (SO) to oxygen and hydrogen peroxide (HOOH) is a superoxide dismutase (SOD). SO is one-electron reduced dioxygen and is both an oxidizing and reducing agent and the source of toxic oxidants like hydroxyl radical. SO will dismutate spontaneously to dioxygen and hydrogen peroxide ($2 O_2^{-1} + 2H^+ \rightarrow O_2 + HOOH$), but it will dismutate 100,000 times more rapidly when catalyzed by SOD. The dismutation of SO leads to the formation of another toxic substance, HOOH, which must be removed by other protective systems. The first of these systems is catalase which converts HOOH into oxygen and water. This process is not believed to be quantitatively important, since mutant red cells, deficient in catalase but with normal amounts of SOD, are stable and do not form methemoglobin or hemolyze easily. Stated another way from a clinical perspective, patients with a deficiency in catalase activity ("acatalasemia") are not seriously affected.

A route for benign HOOH removal is with the enzyme glutathione peroxidase which uses important reducing substrate, GSH. The reaction is $HOOH + 2\ GSH \underset{dase}{\overset{GSH\ peroxi-}{<}} 2\ HOH + GS\text{-}SG$. Patients with GSH-peroxidase deficiency or chronic GSH deficiency are clinically affected, exhibiting methemoglobin, lipid peroxidation and hemolytic anemia. Removal of SO by SOD and HOOH with GSH-peroxidase is metabolically expensive (in terms of loss of NAD(P)H) and GSH levels may fall if oxidative metabolism (hexose monophosphate shunt) cannot supply enough NAD(P)H to recover GSH from GS-SG. The dismutation of superoxide by SOD to oxygen and HOOH and removal of the HOOH with either catalase or GSH-peroxidase leads to the loss of two or four reducing equivalents, respectively. For small amounts of superoxide, this system apparently contributes to the protection of cells and tissues.

Figure 5:
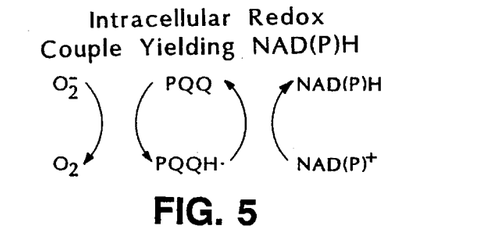
FIG. 5 is a diagram of PQQ-cycled destruction of superoxide.

We have discovered an alternate way in which SO is naturally removed from tissues with a much lower cost in essential reducing equivalents. This mechanism is illustrated in FIG. 5. Here SO is oxidatively catalyzed by PQQ back to dioxygen, without the resulting hydrogen peroxide formation seen after dismutation of superoxide. The PQQ(2H) so generated can then transfer electrons to $NAD(P)^+$, and the NAD(P)H which is reformed can reduce oxidized glutathione (GS-SG) to GSH, with the help of glutathione reductase, to protect the cells. The more PQQ available, the more rapid the recovery of reducing equivalents, the greater the sparing of GSH, and the greater the protection against tissue injury. Accordingly, the rate of superoxide oxidation is augmented by the addition of exogenous PQQ, enhancing protection against oxidative damage caused by oxidative stress and by inflammatory disease, as detailed below.

One example of oxidative stress that can be treated with PQQ is oxidative stress that accompanies reperfusion of tissue that has been subjected to ischemia or loss of blood supply.

In general, reperfusion of tissue that has been subject to ischemia or necrosis leads to oxidative stress. For example, when myocardial tissue has been subject to ischemia or necrosis due to an infarct, and catheterization/angioplasty techniques are use to increase blood flow and oxygen supply to the damaged tissue, there is additional tissue damage associated with oxidative stress incident to reperfusion.

The invention can be used to ameliorate damage from reperfusion injury to myocardial tissue. Similarly, treatment of other infarctions can damage associated tissue, such as ocular thrombosis, bowel infarct, or phlebitis.

Each of these respective conditions can be treated by administering a PQQ/reducing agent combinations as discussed above.

B. Nutrition

As detailed above, PQQ plays a central role in the control of redox states, in vivo, and for that reason, administration of PQQ as a dietary supplement can be beneficial when there is reason to believe that natural mechanisms are not providing adequate amounts of PQQ. For example, prenatal and neonatal administration of PQQ is beneficial, as detailed in co-pending commonly owned U.S. Ser. No. 07/808,187, which is hereby incorporated by reference.

Additionally, for patients who are receiving synthetic alimentation mixtures for sustained periods benefit from administration of PQQ. In particular, patients receiving parenteral nourishment should receive PQQ in combination with a reducing agent according to the invention to maintain a proper oxidative balance. PQQ and a reducing agent are administered in the formulations discussed above in combination with a known hyperalimentation mixture.

C. Chelation Of Heavy Metals

We have also discovered that PQQ has a specific dual benefit in treating heavy metal toxicity, particularly lead, indium and vanadium toxicity. Such toxicity is reportedly attributable at least in part to hemolysis [Hansen et al., *Acta Pharmacol. Toxicol.* (Copenhagen 1986) 59 Suppl. 7 pp. 562–565]and to ATPase inhibition [Richehmi et al. (1989) *Biological Trace Element Research* Vol. 21 pp. 331–335]. Treatment of such poisoning involves vanadium chelation, e.g. with tiron or with D-penicillamine. Domingo et al., *Toxicology* (1980) 62:203–211; Gomez et al., *Toxicol. Letters* (1991) 57.:227–234; Jones et al., *J. Toxicol. and Environ. Health* (1983) 12:749–756.

PQQ is particularly advantageous in this situation because it achieves two simultaneous, reinforcing goals: PQQ chelates the heavy metal toxin and, by mass action, minimizes the ability of the toxin to encounter and complex with endogenous PQQ or with other important compounds. At the same time, exogenous PQQ rectifies the imbalance suffered from loss of native (endogenous) PQQ due to chelation between the toxic metal ligand and native PQQ.

D. Removal Of Undesirable Redox Cycling Pairs

PQQ and an appropriate reducing agent may be used to treat toxicity caused by certain compounds which enable nonproductive redox cycling that generates superoxide radical at the expense of NAD(P)H. Specific compounds that have this effect include certain toxic xenobiotics (e.g., herbicides such as the viologens including paraquat and diquat). Such toxins cause mitochondrial poisoning, resulting in oxidative stress and lipid peroxidative damage. Additionally, impurities such as "NPTP"(1-methyl-4-phenyl1,2,3,6 tetrahydropyridine), an impurity in the street drug popularly known as "angel dust", are known to induce parkinsonism. See Science (1984) 219:979 et seq.; New Eng. J. Med. 309:310 (1983)'and J. Med. Chem. (1985) 28.:997. This condition is a neurological manifestation of the above described SO generation, and it can be treated by administering PQQ with a reducing agent.

PQQ operates by cycling between reducing equivalents and superoxide radical as described in the above section on oxidative stress. In effect, the compounds at issue cause oxidative stress with consequences similar to ischemia and other infarcts mentioned above. PQQ corrects impaired mitochondrial operation, by restoring reducing equivalents, as well as energy via NADPH and glutathione, as described above.

E. Chemotherapy

Common forms of chemotherapy involve administration of anthracycline antitumor agents, with serious side effects. PQQ can ameliorate some of the damaging effects of the chemotherapy.

Specifically, antracycline antibiotics like doxorubucin (adriamycin) have toxic actions on mammalian cells, especially neoplasms. Doxorubicin is one of the most active antineoplastics ever identified. It is used to treat leukemia, Hodgkin's disease and non-Hodgkin's lymphomas, small cell and non-small cell lung cancer, cancers of the breast, ovaries, stomach, thyroid, and bladder, osteogenic and soft tissue sarcomas and malignant melanomas. Toxicities include nausea, vomiting, alopecia, myelosuppression and dose-dependent severe cardiotoxicity.

The potent antitumor action of these agents are derived from their DNA-seeking properties which allow them to intercalate into the DNA-helix promoting interference with neoplasm DNA synthesis. Much of their toxicity for normal tissues, which are relatively less mitotic than neoplasms, is tentatively attributed to direct inhibition of enzyme activity in the mitochondrial respiratory chain, thereby reducing the level of ATP below that necessary for cardiac function, release of histamine and catecholamines with resultant myocardial damage, inhibition of RNA synthesis, selective inhibition of the mitochondrial calcium pump, and free radical generation with resultant lipid peroxidation. See generally, Zidendrg-Cherr et al. Toxicology Letters, (1986) 30:79–87.

We propose that a significant degree of such toxicity arises from the fact that antracycline agents undergo repetitive oxidation-reduction (redox-cycling) and form superoxide anion, the precursor of toxic radical oxidants:

$2\ O_2 + 2H$ (cellular reducing agents)—doxorubicin→$2\ O_2^- + 2H+$

PQQ can oxidatively remove unwanted superoxide from tissues and transfer captured electrons back into the cellular pool of protective reducing compounds like NAD(P)H and reduced glutathione. See FIG. 2, which shows that antitumor agents like doxorubicin catalyze the formation of superoxide, and superoxide can be oxidatively removed by the PQQ/Ascorbate system. The electrons gained from superoxide are eventually used to regenerate reduced glutathione and are shuttled from PQQ/Ascorbate through flavo-enzymes (E-FADH$_2$) and NAD(P)H. The system is an NAD(P)H oxidase driven to the left in FIG. 2 by the excess superoxide generated and oxidized by PQQ. The rate of superoxide removal is accelerated by adding PQQ. As described above the antioxidant action of PQQ depends on its ability to catalyze the conversion of superoxide to dioxygen with a concomitant reduction of the oxidized quinoneform of PQQ to both its semiquinone and hydroquinone forms. These reduced forms of PQQ shuttle electrons to NAD(P)+ and reform NAD(P)H in a natural redox cycle designed by nature to replenish the level of the key protective reducing agents in cells, especially reduced glutathione (GSH). The rate in which the replenishment of GSH occurs depends on the concentration of PQQ. Pharmacologically active, non-toxic levels of PQQ can be obtained by IP injection of PQQ or by oral administration of PQQ, as described above.

Figure 2:
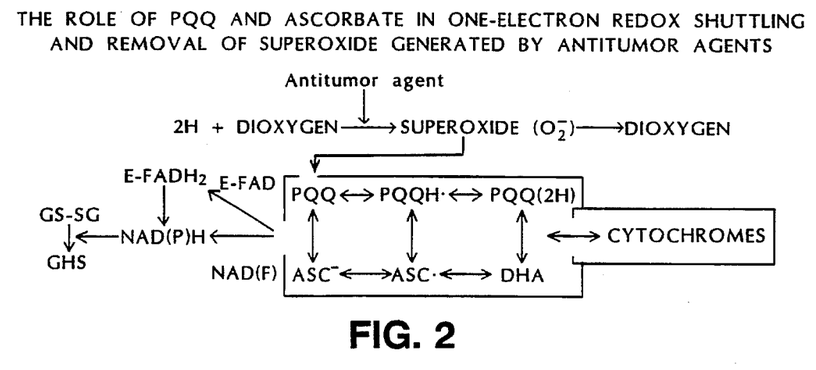
FIG. 2 is a diagram of additional redox reactions involving PQQ.

Since PQQ is naturally present in mammals, the pharmacological doses necessary to protect cancer patients against the redox-side reactions of antitumor agents are more likely to be non-toxic and to be well tolerated. As noted above, PQQ works in concert with ascorbate forming a redox cycle through which superoxide is removed, dioxygen formed, and NAD(P)H and GSH regenerated. This pathway is shown in FIG. 2. The rate of electron scavenging from superoxide anion depends directly on the concentration of PQQ.

PQQ, or PQQ plus reducing agent(s) such as ascorbate be used as an therapeutic adjunct during doxorubicin anticancer therapy. PQQ in pharmacological amounts will reduce the toxic side effects of redox-cycling antitumor agents, because of PQQ's catalytic removal of toxic oxidants derived from superoxide and formed as unwanted toxic side products by doxorubicin and related agents. We believe that this is particularly relevant to long term cardiac side effects. Cardiotoxicity often limits dose elevation and results in severe morbidity. Cardiotoxicity is frequently life-threatening, even when the primary neoplasm has been removed. For the PQQ/ascorbate combination, the absence of toxicity is demonstrated by the presence of both components in human milk and colostrum.

PQQ can also be used to ameliorate undesired effects of other chemotherapeutic agents which operate by unproductive redox cycling generating SO.

F. Antiinflammatory

The importance of the above-described reactions involving PQQ and superoxide and the role of PQQ becomes especially important when inflammatory diseases occur. Inflammation may arise immunologically from foreign agents or originate from autoimmune reactions. Other sources of inflammation are ischemia, or it may arise from drugs or radiation. The role of pharmacological amounts of PQQ in accelerating the reaction in Formula 1 (above) to the left, in order to decrease the release of toxic oxidants from excessively committed immune cells Inflammatory reactions in, or close to, connective tissues, produce toxic oxidants which cause extensive irreversible tissue damage. Important structural connective tissue proteins like collagen are degraded. Mucopolysaccharides like hyaluronic acid are also degraded with the loss of the viscosity and joint-lubricant properties required of normal synovial fluid.

In order to protect against oxidant damage, past protocols have been proposed based on the use of superoxide dismutase to remove superoxide. Older protocols were also based on the use of then known antioxidant agents. Adding pharmacological amounts of reduced PQQ, a substance already present in cells and tissues in physiological amounts amplifies natural protective mechanisms. We propose that extra PQQ enters the inflammatory cells which are low in reducing equivalents since they have been used to generate SO from dioxygen. By changing the equilibrium direction of Formula 1 from the right to the left at the expense of superoxide oxidation by PQQ, excessive radical oxygen formation ceases with regeneration of increased NAD(P)H and the reformation of protective amounts of GSH also recurs. See FIG. 5.

The invention for the therapy of inflammatory joint disease or rheumatoid arthritis, exposes the inflamed areas to PQQ(2H) (PQQ in its reduced or hydroquinone form) delivered locally by injection or by iontophoresis. In addition, PQQ(2H) can be added globally by systemic injection of pharmacological levels. The invention also proposes that iontophoresis of PQQ(2H), a highly negatively charged, trianionic compound, be used to deliver PQQ(2H) to locally inflamed areas. PQQ(2H) is obtained from PQQ with ascorbate and thiol compounds such as D-penicillamine or mercaptosuccinate. Other agents such as glycine or dopamine can also be used. As described above, Tiron® or D-penicillamine can also be used.

Normally, in the extracellular fluid present in most tissue including the synovial fluid which surrounds and lubricates joints, a very important antioxidant is present in large concentrations, usually over 1 millimolar. This antioxidant is ascorbic acid in its anionic form, known as ascorbate. Ascorbate is a potent reducing aging and serves to keep extracellular PQQ in it reduced, less reactive hydroquinone form, PQQ(2H). Ascorbate anion can be oxidized to uncharged dehydroascorbate. In normal synovial fluid, Laennec and Blake (1989) Free Radical Res. Commun 1:31–39 have found that the ratio of ascorbate to dehydroascorbate is very high. This indicates and that extracellularly, a reducing environment is maintained by the ascorbate in formal synovial fluid. Laennec and Blade have also shown for the first time that the synovial fluid ascorbate/dehydroascorbate ratio becomes inverted when severe inflammatory joint disease is present. This indicates that the inflammatory process has produced so much radical oxidants that the high extracellular levels of ascorbate has been depleted by oxidation. PQQ(2H) should be added to the inflamed joint in an excess of ascorbate.

Glucose may also be added. Injected PQQ(2H) and glucose is taken up by the cells present. Here, added glucose supplies fuel for the functioning cells so that additional NADPH and GSH can be regenerated. PQQ, maintained in reduced form extracellularly by ascorbate enters the cells which are deficient in reducing equivalents and as the natural redox catalyst now present in higher concentration in the involved cells, rapidly accelerates superoxide oxidation, removing electrons by the oxidation of superoxide and shuttling it back into the protective reducing economy of the cells as NADPH and then GSH. Since both PQQ(2H) and ascorbate are anionic, they can be delivered together into inflamed joints by iontophoresis. Dehydroascorbate, which is not wanted is uncharged and will not iontophorize into tissues.

Greenwald (1991) Seminars in Arthritis and Rheumatism 20:219–240 have reviewed the damage caused to connective tissue by the oxidative stress of inflammation. It appears from a vast amount of evidence that oxygen-derived free radicals, derived from superoxide and from hydrogen peroxide mediate inflammatory process with lead to tissue destruction. Radical oxidants are derived from activated phagocytes and transition metals play an important role in transmutation of superoxide into more toxic products. Radical oxidants clearly degrade hyaluronic acid, oxidize and otherwise modify collagen and proteoglycans, and interact with and alter immunoglobulin. There may be enough scavenging initiated by dismutation to limit the tissue and cell damage caused by mild states of inflammation, and non-steroidal antioxidant drugs and antiinflammatory agents may be helpful in these cases. However, PQQ's powerful anti-oxidative power is particularly helpful in treating more sever inflammatory disease.

In sum, PQQ generally can be used with a reducing agent to treat connective tissue and organ inflammatory and degenerative conditions. Conditions to be treated include not only inflammatory arthritis, but also joint disease (osteoarthritis), arthritis due to injury and trauma of all kinds; myositis, tendosynovitis, tendonitis, bursitis including calcific bursitis, scleroderma, fascitis including Dupuytren's Disease, carpel tunnel syndrome; also, the combination can be used to treat conditions including excess production of healing tissues such as occurs in the healing response known as "hypertrophic scarring" and the formation of keloids.

G. Methemoglobinemia

Figure 6:
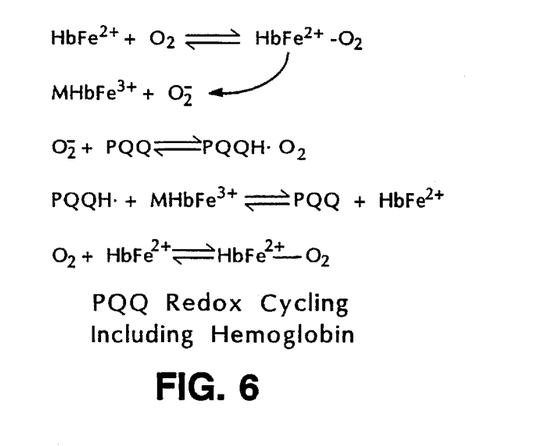
FIG. 6 is a diagram of PQQ-cycled destruction of methemoglobin and superoxide.

FIG. 6 shows intracellular redox couples involving hemoglobin. Specifically, it is well known that hemoglobin ($HbFe^{2+}$)) is reversibly oxygenated to yield oxyhemoglobin ($HbFe^{2+}-O_2$), the important carrier of oxygen to all tissues of the body. Oxyhemoglobin is unstable and irreversibly dissociates into methemoglobin ($MHb(Fe^{3+})$)) and superoxide radical ($O_2^-$). A known enzymatic mechanism for coping with these potentially toxic products involves methemoglobin reductase, which consumes NAD(P)H to yield hemoglobin, $H^+$ and $NAD(P)^+$.

It is also known that defects in this process (e.g. defects in the enzyme methemoglobin reductase) produce a condition in which methemoglobin is found in circulating blood. Some current therapies focus on enhancing the above enzymatically catalyzed process by removing superoxide radical and shifting the equilibrium of the reaction.

We have recognized that PQQ will accomplish that goal, as well as accomplishing a significant additional goal simultaneously. PQQ will non-enzymatically remove SO by the mechanism described in FIG. 6. Specifically, PQQ removes $O_2^-$ as described above yielding $O_2$ and PQQH·. Advantageously, the PQQH· thus formed will reduce methemoglobin to reform PQQ and hemoglobin ($Fe^{2+}$). The $O_2$ formed in the removal of SO may then combine with hemoglobin to yield the desired oxyhemoglobin.

PQQ therefore is useful to treat not only standard methemoglobinemia but also in clinical situations where methemoglobinemia has been induced by exposure to toxins or therapeutics such as nitrites, malaria drugs (e.g., primaquine), sulfonamides and others. PQQ is also useful to treat defects in red cells resulting from deficiencies in glucose-6-phosphate dehydrogenase or 6-phosphogluconate dehydrogenase. These deficiencies lead to conditions which disrupt the ability of red cells to reduce oxidized glutathione.

H. Anti-Alcohol Toxicity

PQQ has been proposed as treatment for alcohol toxicity. Hobara et al., cited above, hereby incorporated by reference. Moreover, we have shown that removal of acetaldehyde, when accomplished by xanthine oxidase, yields superoxide which is responsible for a significant amount of the toxicity of acetaldehyde. We have also shown that the same enzyme, in combination with PQQ, is a dehydrogenase (xanthene dehydrogenase) which removes acetaldehyde without yielding SO. The PQQ/reducing agent combinations described herein represent a significant improvement to existing treatments of alcohol toxicity.

I. Cataract Treatment

PQQ has also been proposed as a cataract treatment. Nishigori et al., cited above, hereby incorporated by reference. The PQQ/reducing agent combinations described herein may be topically administered to treat cataracts in the manner generally described by Nishigori et al.

J. Ionizing Radiation

It is known that ionizing radiation toxicity is caused at least in part by oxidative processes involving SO. In particular, radiational cancer/tumor therapies have serious side effects related to generation of SO. PQQ can ameliorate undesired effects of ionizing radiation by removing SO as described above.

Other embodiments are within the following claims.

What is claimed is:

1. A method for complexing a heavy metal in a patient in need thereof and/or increasing PQQ levels in said patient, said method comprising administering to said patient a therapeutically effective amount of 2,7,9-tricarboxypyrroloquinoline quinone.

2. The method of claim 1 wherein said heavy metal is lead.

3. The method of claim 1 in which said heavy metal is indium.

4. The method of claim 1 in which said heavy metal is vanadium.

* * * * *

UNITED STATES PATENT AND TRADEMARK OFFICE
CERTIFICATE OF CORRECTION

PATENT NO. : 5,460,819
DATED : October 24, 1995
INVENTOR(S) : Gallop et al.

It is certified that error appears in the above-indentified patent and that said Letters Patent is hereby corrected as shown below:

Title page, Col. 2,

In the References Cited section, in the Tsuchida reference, "(QPQ)" should be --(OPQ)--.

Col. 1, line 7, after "invention." start a new paragraph with "This".

Col. 4, line 35, after "agent" start a new paragraph with "PQQ".

Col. 5, line 30, after "excess" insert a period

Col. 8, line 18, "$O_2{}^{31}$" should be --$O_2{}^-$--.

Col. 9, line 41, "57.:227-234" should be --57:227-234--; line 65, "28.:997" should be --28:997--.

Col. 11, line 11, "an" should be --a--

Signed and Sealed this

Thirteenth Day of August, 1996

Attest:

BRUCE LEHMAN

*Attesting Officer*     Commissioner of Patents and Trademarks